(12) United States Patent
Ingber et al.

(10) Patent No.: US 10,656,140 B2
(45) Date of Patent: *May 19, 2020

(54) SYSTEM FOR CONDUCTING THE IDENTIFICATION OF BACTERIA IN URINE

(71) Applicant: POCARED Diagnostics LTD., Rehovot (IL)

(72) Inventors: Gal Ingber, Oranit (IL); William G. Atterbury, Columbus, OH (US); Russell H. Barnes, Columbus, OH (US); Douglas E. Boyd, Dublin, OH (US); Joseph D. Dennis, Grandview Heights, OH (US); Jonathan Gurfinkel, Omer (IL); Dave Holley, Lancaster, OH (US); Steven E. Huckaby, Columbus, OH (US); Thomas A. Klausing, Powell, OH (US); John S. Laudo, Columbus, OH (US); Kevin Sadeski, Canal Winchester, OH (US); Jason A. Schaefer, Plainfield, IN (US); K. Bryan Scott, Westerville, OH (US); Carol Stillman, Lewis Center, OH (US); Sherwood Talbert, Columbus, OH (US); John Tallarico, Powell, OH (US)

(73) Assignee: POCARED Diagnostics LTD., Rehovot (IL)

(*) Notice: Subject to any disclaimer, the term of this patent is extended or adjusted under 35 U.S.C. 154(b) by 390 days.

This patent is subject to a terminal disclaimer.

(21) Appl. No.: 15/425,253

(22) Filed: Feb. 6, 2017

(65) Prior Publication Data

US 2017/0146515 A1 May 25, 2017

Related U.S. Application Data (60) Division of application No. 14/330,450, filed on Jul. 14, 2014, now Pat. No. 9,606,105, which is a (Continued)

(51) Int. Cl.
*G01N 35/02* (2006.01)
*G01N 33/493* (2006.01)
(Continued)

(52) U.S. Cl.
CPC ............ *G01N 33/493* (2013.01); *C12Q 1/04* (2013.01); *G01N 21/0303* (2013.01);
(Continued)

(58) Field of Classification Search
CPC .............. G01N 35/025; G01N 35/026; G01N 2035/0439; G01N 2035/0444
See application file for complete search history.

(56) References Cited

U.S. PATENT DOCUMENTS

| 3,849,654 A | 11/1974 | Malvin |
| 4,360,360 A | 11/1982 | Chiknas |

(Continued)

FOREIGN PATENT DOCUMENTS

| CN | 201464472 U | 5/2010 |
| EP | 0637283 A1 | 2/1995 |

(Continued)

OTHER PUBLICATIONS

Giana et al.; "Rapid Identification of Bacterial Species by Fluorescence Spectroscopy and Classification through Principal Components Analysis"; Journal of Fluorescence; 2003; pp. 489-493; vol. 13:6.

(Continued)

*Primary Examiner* — Jill A Warden
*Assistant Examiner* — Dwayne K Handy
(74) *Attorney, Agent, or Firm* — The Webb Law Firm

(57) ABSTRACT

A system for conducting the identification and quantification of micro-organisms, e.g., bacteria in urine samples which includes: 1) several disposable cartridges for holding four disposable components including a centrifuge tube, a pipette tip having a 1 ml volume, a second pipette tip having a 0.5 ml volume, and an optical cup or cuvette; 2) a sample processor for receiving the disposable cartridges and processing the urine samples including transferring the processed urine sample to the optical cups; and 3) an optical analyzer for receiving the disposable cartridges and configured to analyze the type and quantity of micro-organisms in the urine sample. The disposable cartridges with their components including the optical cups or cuvettes are used in the sample processor, and the optical cups or cuvettes containing the processed urine samples are used in the optical analyzer for identifying and quantifying the type of micro-organism existing in the processed urine samples.

18 Claims, 11 Drawing Sheets

Related U.S. Application Data continuation of application No. 12/682,402, filed as application No. PCT/US2008/079533 on Oct. 10, 2008, now Pat. No. 8,808,649.

(60) Provisional application No. 60/978,810, filed on Oct. 10, 2007, provisional application No. 60/978,862, filed on Oct. 10, 2007, provisional application No. 60/978,856, filed on Oct. 10, 2007, provisional application No. 60/978,820, filed on Oct. 10, 2007.

(51) Int. Cl.
  *C12Q 1/04* (2006.01)
  *G01N 21/03* (2006.01)
  *G01N 35/04* (2006.01)
  *G01N 21/64* (2006.01)

(52) U.S. Cl.
  CPC ........... *G01N 35/025* (2013.01); *G01N 35/04* (2013.01); *G01N 2021/6482* (2013.01); *G01N 2035/0436* (2013.01); *G01N 2035/0444* (2013.01); *G01N 2035/0448* (2013.01); *G01N 2035/0458* (2013.01); *G01N 2201/0415* (2013.01)

(56) References Cited

U.S. PATENT DOCUMENTS

| | | | |
|---|---|---|---|
| 4,406,547 A | | 9/1983 | Aihara |
| 4,477,186 A | | 10/1984 | Carlson |
| 4,509,856 A | | 4/1985 | Lee |
| 4,556,636 A | | 12/1985 | Belly et al. |
| 4,873,993 A | | 10/1989 | Meserol et al. |
| 4,918,984 A | | 4/1990 | Martinoli et al. |
| 5,314,825 A | | 5/1994 | Weyrauch et al. |
| 5,424,036 A | | 6/1995 | Ushikubo |
| 5,578,269 A | | 11/1996 | Yaremko et al. |
| 5,605,665 A | | 2/1997 | Clark et al. |
| 5,700,428 A | | 12/1997 | Carlson |
| 5,762,878 A | * | 6/1998 | Clark ............... B01F 11/0022 206/459.5 |
| 5,855,847 A | * | 1/1999 | Oonuma ............. G01N 35/02 422/63 |
| 5,866,072 A | | 2/1999 | Bowe, Jr. et al. |
| 6,515,745 B2 | | 2/2003 | Vurens et al. |
| 6,559,941 B1 | | 5/2003 | Hammer |
| 6,602,474 B1 | | 8/2003 | Tajima |
| 6,767,511 B1 | | 7/2004 | Rousseau |
| 6,773,922 B2 | | 8/2004 | Jeng et al. |
| 7,206,620 B2 | | 4/2007 | Erickson et al. |
| 7,277,175 B2 | | 10/2007 | Thompson et al. |
| 7,299,079 B2 | | 11/2007 | Rebec et al. |
| 7,303,922 B2 | | 12/2007 | Jeng et al. |
| 7,959,878 B2 | | 6/2011 | Rousseau |
| 8,808,649 B2 | * | 8/2014 | Ingber ............... C12Q 1/04 422/554 |
| 2002/0149768 A1 | * | 10/2002 | Sabsabi ............. G01N 21/15 356/318 |
| 2003/0116497 A1 | | 6/2003 | Carlson et al. |
| 2004/0159798 A1 | | 8/2004 | Martin et al. |
| 2005/0110980 A1 | | 5/2005 | Maehara et al. |
| 2005/0110989 A1 | | 5/2005 | Schermer et al. |
| 2005/0175502 A1 | | 8/2005 | Rousseau et al. |
| 2005/0271550 A1 | | 12/2005 | Talmer et al. |
| 2006/0013729 A1 | | 1/2006 | Carey et al. |
| 2006/0120926 A1 | | 6/2006 | Takada et al. |
| 2007/0037135 A1 | | 2/2007 | Barnes et al. |
| 2007/0189925 A1 | | 8/2007 | Blecka et al. |
| 2007/0224083 A1 | | 9/2007 | Ouchi et al. |
| 2008/0003665 A1 | | 1/2008 | Potyrailo et al. |
| 2008/0297796 A1 | | 12/2008 | Lukas et al. |
| 2008/0297798 A1 | | 12/2008 | Wyssen |
| 2009/0067280 A1 | | 3/2009 | Ammann et al. |
| 2010/0208256 A1 | | 8/2010 | Tang et al. |
| 2014/0065646 A1 | | 3/2014 | Holtlund et al. |

FOREIGN PATENT DOCUMENTS

| | | |
|---|---|---|
| EP | 0649534 A1 | 4/1995 |
| EP | 1679501 A2 | 7/2006 |
| EP | 1691201 A2 | 8/2006 |
| GB | 2019563 A | 10/1979 |
| JP | 54073092 A | 6/1979 |
| JP | 57186153 A | 11/1982 |
| JP | 6266141 A | 3/1987 |
| JP | 62135965 U | 8/1987 |
| JP | 6463869 A | 3/1989 |
| JP | 1105849 U | 7/1989 |
| JP | 64065458 A | 10/1989 |
| JP | 235367 A | 2/1990 |
| JP | 02228562 A | 9/1990 |
| JP | 2254364 A | 10/1990 |
| JP | 03181853 A | 8/1991 |
| JP | 436197 A | 2/1992 |
| JP | 6113887 A | 4/1994 |
| JP | 07505474 A | 6/1995 |
| JP | 7236838 A | 9/1995 |
| JP | 08122336 A | 5/1996 |
| JP | 9119926 A | 5/1997 |
| JP | 9505669 A | 6/1997 |
| JP | 09507917 A | 8/1997 |
| JP | 11316189 A | 11/1999 |
| JP | 2001159633 A | 6/2001 |
| JP | 2001318101 A | 11/2001 |
| JP | 2002286553 A | 10/2002 |
| JP | 2003177138 A | 6/2003 |
| JP | 2003270146 A | 9/2003 |
| JP | 2003344290 A | 12/2003 |
| JP | 2004203390 A | 7/2004 |
| JP | 2004531725 A | 10/2004 |
| JP | 2005010179 A | 1/2005 |
| JP | 2005526252 A | 9/2005 |
| JP | 2005291954 A | 10/2005 |
| JP | 2006500302 A | 1/2006 |
| JP | 2006511803 A | 4/2006 |
| JP | 2006208139 A | 8/2006 |
| JP | 2006226887 A | 8/2006 |
| JP | 2007003401 A | 1/2007 |
| JP | 2007178328 A | 7/2007 |
| JP | 2006220494 A | 8/2008 |
| JP | 2008224686 A | 9/2008 |
| WO | 9310454 A1 | 5/1993 |
| WO | 9319928 A1 | 10/1993 |
| WO | 9320440 A2 | 10/1993 |

(56) References Cited

FOREIGN PATENT DOCUMENTS

| WO | 9320444 A1 | 10/1993 |
| WO | 2004055522 A1 | 7/2004 |
| WO | 2005008255 A1 | 1/2005 |
| WO | 2005124365 A2 | 12/2005 |
| WO | 2007039524 A2 | 4/2007 |
| WO | 2007047814 A2 | 4/2007 |
| WO | 2007085715 A1 | 8/2007 |
| WO | 2009049171 A2 | 4/2009 |
| WO | 2009100197 A2 | 8/2009 |

OTHER PUBLICATIONS

Zhao et al.; "A rapid bioassay for single bacterial cell quantification using bioconjugated nanoparticles"; Proceedings of the National Academy of Sciences; National Academy of Sciences, US; vol. 101:42; Oct. 19, 2004; pp. 15027-15032; XP003013080; ISSN: 0027-8424; DOI: 10.1073/PNAS.0404806101.

* cited by examiner

SYSTEM FOR CONDUCTING THE IDENTIFICATION OF BACTERIA IN URINE

CROSS REFERENCE TO RELATED APPLICATIONS

The present application claims priority as a divisional application of U.S. patent application Ser. No. 14/330,450 entitled "System for Conducting the Identification of Bacteria in Urine" filed Jul. 14, 2014, which claims priority to U.S. patent application Ser. No. 12/682,402 entitled "System For Conducting The Identification Of Bacteria In Urine" filed Sep. 15, 2010, now U.S. Pat. No. 8,808,649, which is the United States national phase of International Patent Application No. PCT/US2008/079533 entitled "System For Conducting The Identification Of Bacteria In Urine" filed Oct. 10, 2008, which claims priority to U.S. Provisional Application Nos. 60/978,810, 60/978,820, 60/978,856 and 60/978,862, all filed on Oct. 10, 2007, which are herein incorporated by reference in their entirety.

BACKGROUND OF THE INVENTION

Field of the Invention

The present invention relates to a system for conducting the identification and quantification of micro-organisms, e.g., bacteria in urine samples. More particularly, the invention relates to a system for identifying bacteria in urine samples which includes: 1) a disposable cartridge or holder for holding disposable components including a centrifuge tube, two pipette tips with a different volume capacity, and an optical cup or cuvette; 2) a sample processor for processing or preparing the urine samples; and 3) an optical analyzer for analyzing the processed urine samples. The disposable cartridge with its four components is used in the sample processor and the optical cup or cuvette in particular is used in the optical analyzer.

Description of Related Art

In general, current-day practice for identifying micro-organisms, e.g., bacteria in urine samples involves a complex, lengthy and expensive process for identifying and specifying micro-organisms in microbiology labs. In the current process, the samples are accepted into the lab. These specimens are then sorted and labeled and then they are inoculated onto blood agar medium using sterilized loop. The specimens are then inserted into a dedicated incubator for a 24-hour period. A day later, the lab technicians screen the specimens for positive and negative cultures. In general, most of the cultures are negative and they are manually reported. The organisms for the positive cultures are isolated and suspended in a biochemical fluid. This involves suspension, dilution, vortexing and turbidity measurements resulting in biochemical waste products. The cultures are then subjected to a species identification and antibiotics susceptibility testing exposing the suspensions to multiple reagents. After another 6 to 24-hour incubation period, the findings are interpreted and reported by lab technicians. This entire process generally takes 11 steps and 50 hours to obtain specimen results and the process is labor intensive.

Commonly owned U.S. Publication No. US 2007/0037135 A1, the contents of which are herein incorporated by reference, discloses a system for identifying and quantification of a biological sample suspended in a liquid. Paragraph [0038] of this publication states that sample cuvettes are used. These cuvettes are said to be well known in the art and are typically square or rectangular in shape (having a well area to contain the sample) and are made of a transparent material such as glass or a polymeric material.

There is a need, therefore, particularly for species identification of the above lab procedure to provide a more efficient, and less time consuming process which requires less labor.

SUMMARY OF THE INVENTION

The system of the invention streamlines this current system for obtaining specimen results. The system is environmentally friendly, enables a rapid diagnosis, results are consistent, no reagents are needed and there is a multifunctional diagnosis. Urine samples are contained within disposable cartridges which hold four disposable components, i.e., a centrifuge, two pipette tips with a different volume and an optical cuvette. The cartridges are bar coded and tied in with the patient's ID. The cartridges are inserted in a magazine which is then inserted into a sample processor which processes the specimens. The prepared specimens are transferred into the optical cuvettes and then the magazine is inserted into an optical analyzer which analyses the specimens. The optical analyzer analyses and generates the complete results enabling ultimate treatment of the bacteria. The system does not require a sophisticated operator and gives rapid results. The system increases efficiency, improves workload, saves time and money and is easy to operate. The sample preparation can be performed in parallel with the specimen analysis process and from 1 to 50 specimens can be analyzed simultaneously.

The system includes a plurality of disposable cartridges for holding a plurality of disposable components including a centrifuge tube, a first pipette tip with a 1 ml volume; an optical urine sample cuvette, and a second pipette tip with a 0.5 ml volume; a sample processor for receiving the plurality of disposable cartridges and configured to process and prepare the urine sample of each disposable cartridge and to transfer the urine samples into the respective optical cuvette of each of the disposable cartridges; and an optical analyzer for receiving the cartridge with the optical cuvettes containing the processed urine samples and analyzing and generating the specimen results. The entire process of processing the urine specimens in the sample processor and analyzing them in the optical analyzer takes about 20 minutes for a single specimen and up to 2 hours for 50 specimens.

The disposable cartridge and the disposable components increase efficiency, improve workload and save time and money since the components necessary for the preparation or processing of the urine samples are conveniently located in one place, i.e., in a cartridge. Additionally, less manpower or manual handling of the components is required for the processing/analyzing of the urine samples. There is also the added convenience in that the cartridge and its components are disposable. That is, these items do not need to be sterilized for the next urine specimen identification process and contamination of the work area and/or surrounding environment is minimized.

The sample processor of the invention streamlines the current practice for processing urine samples for analysis. The sample processor of the invention is automated, fully compact, self-contained and does not require any reagents. Urine samples are injected into centrifuge tubes which are carried in removable cartridges. The specimens are bar coded and tied with the cartridges which are also bar coded. The cartridges are mounted in a magazine which is then inserted into the sample processor which processes the specimens in preparation for analysis. The sample processor does not require a sophisticated operator and rapidly processes the samples or specimens. The sample processor increases efficiency, improves workload, saves time and money and is easy to operate. The processing of several samples can be performed in about 20 minutes for a single specimen and up to 1 hour for about 50 specimens.

The optical analyzer contains an optics system, a thermal control and a drawer which has a rotatable table for receiving, supporting and rotating a magazine containing a plurality of disposable cartridges with optical cups or cuvettes which contain the urine samples to be analyzed. The optical analyzer also contains a bar code reader for inventorying the urine samples and a level sensor that verifies that each optical cup or cuvette contains the correct volume of processed urine sample. When the drawer with the magazine is inserted into the optical analyzer, the drive mechanism for the rotatable table supporting the magazine rotates and registers the magazine relative to the bar code reader and then rotates and registers the magazine relative to the optics system. The optics system includes an excitation module unit, an optical collection unit and a spectrometer. The temperature of each cup or cuvette is decreased to a temperature which will slow the metabolism of the bacteria in the urine samples while increasing the fluorescence signal. A thermal control cools a large thermal mass which is located on the rotatable table underneath the magazine containing the disposable cartridges with urine sample cups or cuvettes. An infrared temperature sensor detects and monitors the temperature of each urine sample.

A related method for identifying the type of microorganism and quantifying it in a urine sample includes the steps of obtaining a urine sample; passing the urine sample through a ten micron filter; obtaining a 2 ml sample of the filtered urine and placing it into a centrifuge tube; obtaining a 1,000,000:1 dilution of the dissolved materials in the urine retaining bacteria in the urine sample by centrifuging the 2 ml sample at about a 12,000 g-force, decanting about 95% of the fluid in the centrifuge tube, replacing the decanted solution with a saline solution, and repeating these steps about five times; transferring the final solution into an optical cup or cuvette; and subjecting the optical cup or cuvette to an optical analysis having optics which include exciting the urine sample with at least five different wavelengths, collecting and detecting the fluorescent emissions; and directing the fluorescent emissions into a spectrometer.

These and other objects and advantages of the invention will be made apparent from the following description taken together with the drawings.

DETAILED DESCRIPTION OF THE INVENTION

The present invention will be described with reference to the accompanying drawings where like reference numbers correspond to like elements.

Figure 1A:
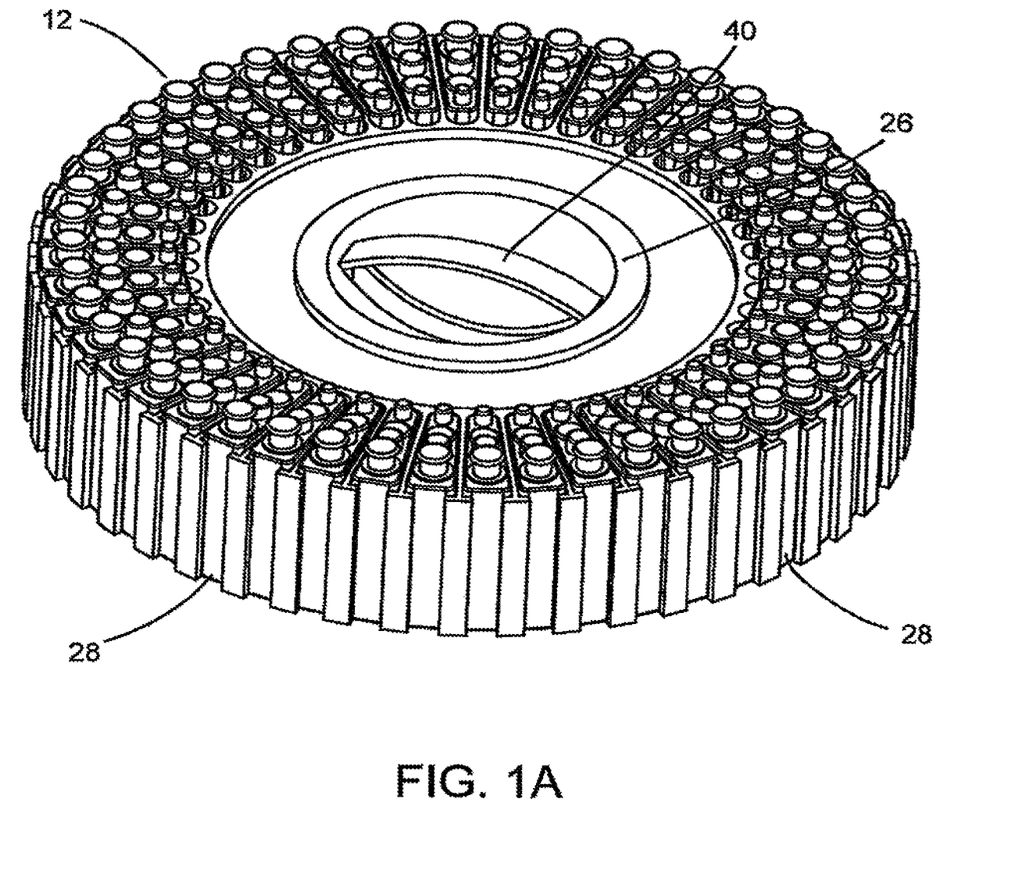
FIG. 1A is a top perspective view of a magazine having a plurality of disposable cartridges.
Figure 1B:
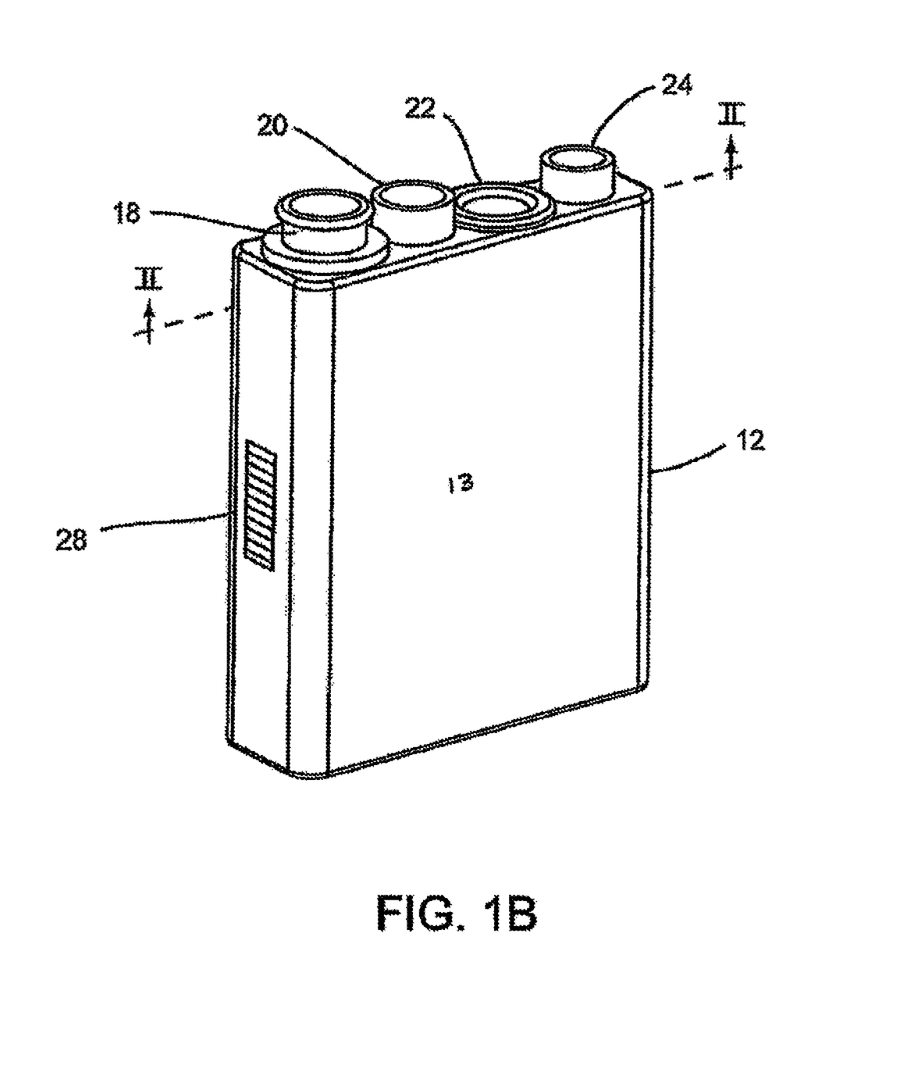
FIG. 1B is a top perspective view of a disposable cartridge used in the magazine shown in FIG. 1A.
Figure 2:
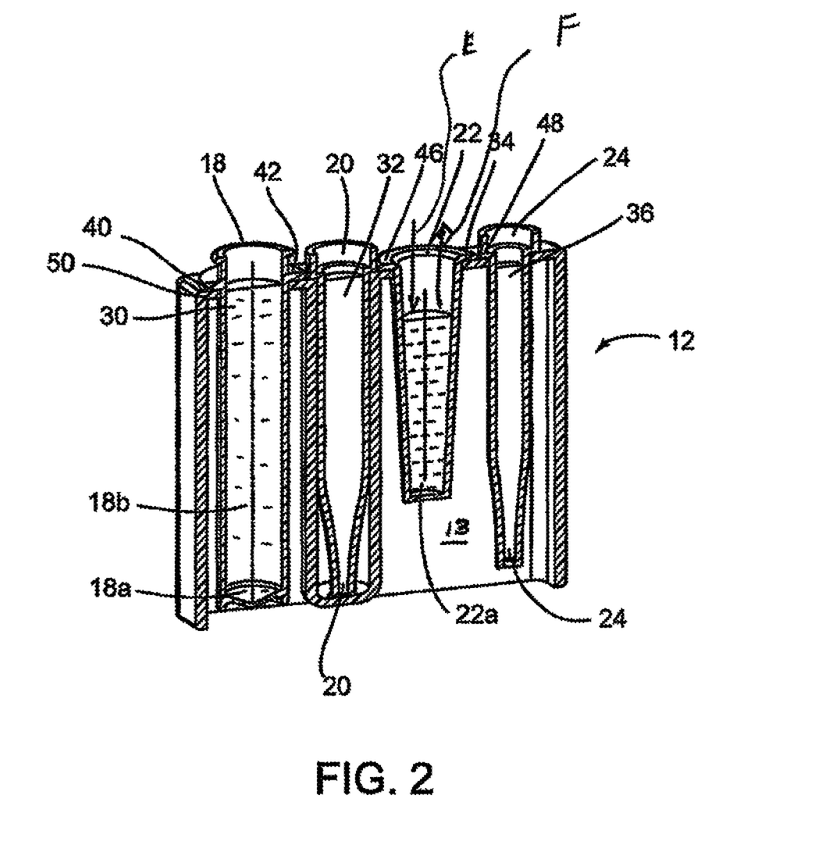
FIG. 2 is a front sectional view illustrating the components of the disposable cartridge of FIG. 1 in phantom.
Figure 3A:
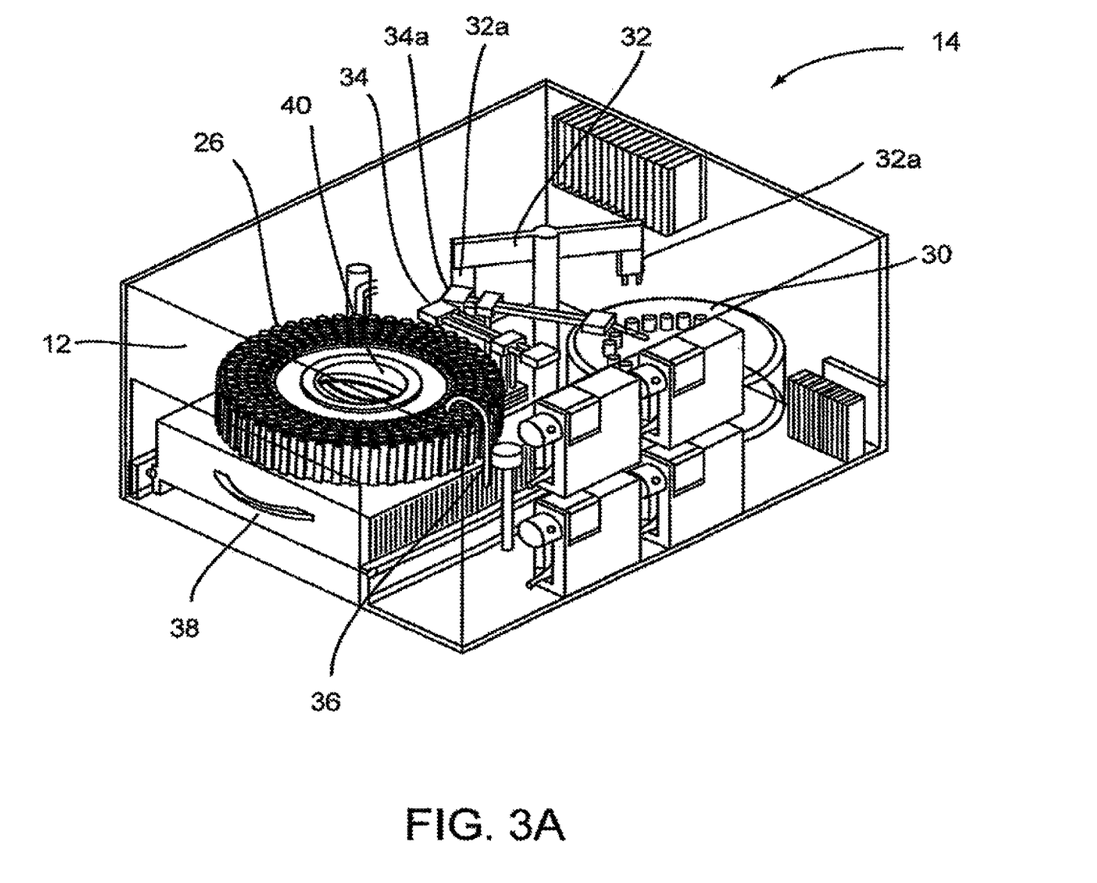
FIG. 3A is a perspective view of a sample processor illustrating in phantom the several components of the sample processor of the system of the invention.
Figure 3B:
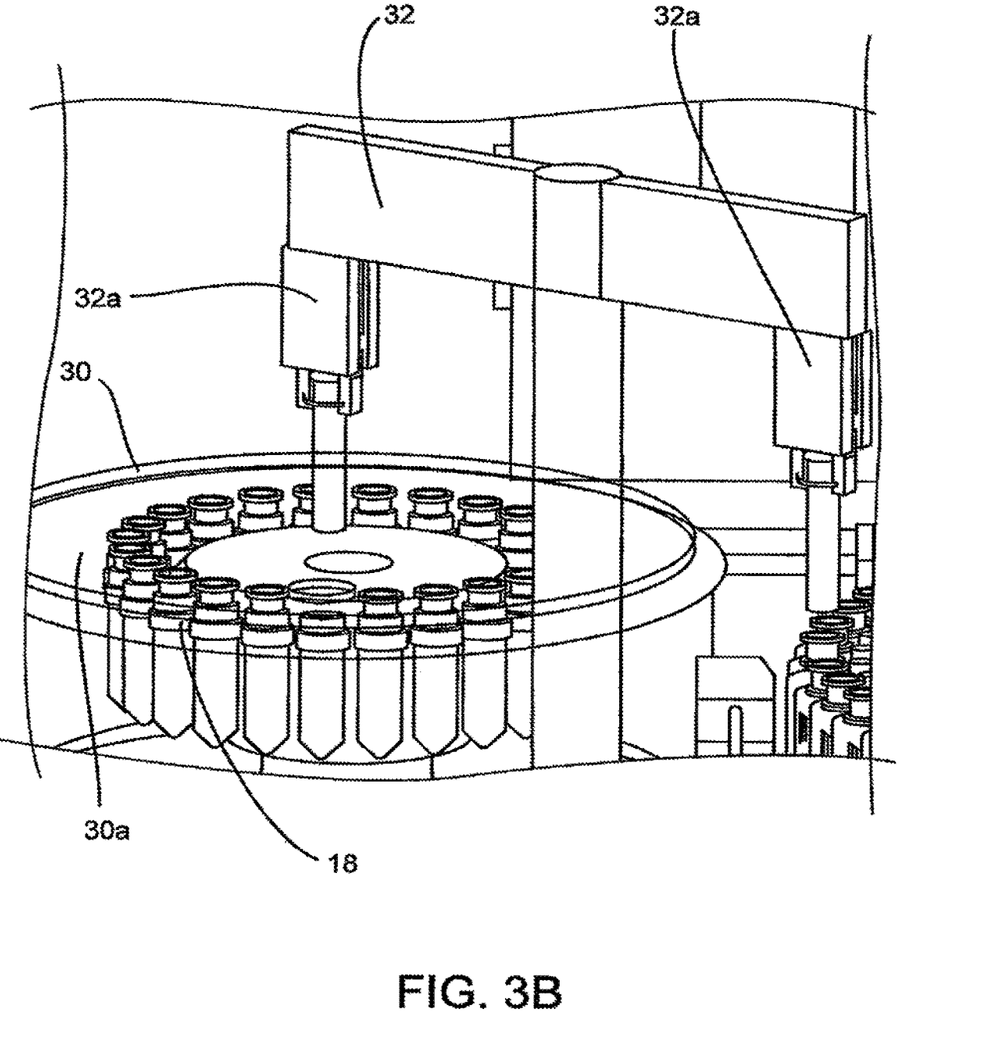
FIG. 3B is an additional perspective view of a sample processor illustrating in phantom the several components of the sample processor of the system of the invention.
Figure 4A:
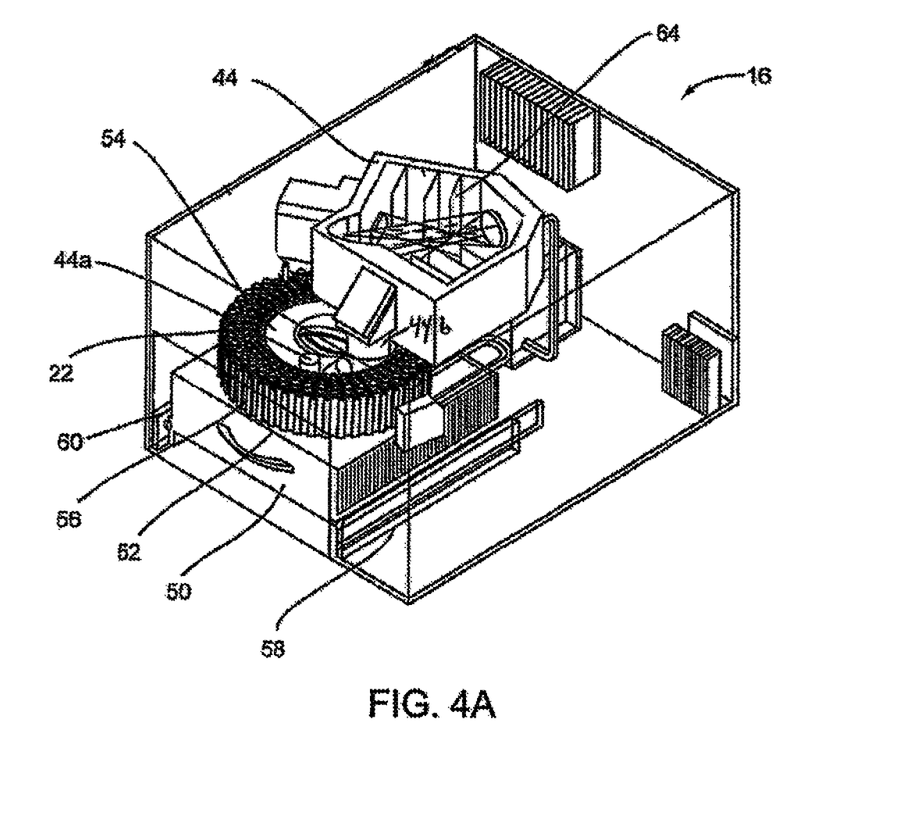
FIG. 4A is a perspective view of an optical analyzer illustrating in phantom the several components of the optical analyzer of the system of the invention.
Figure 4B:
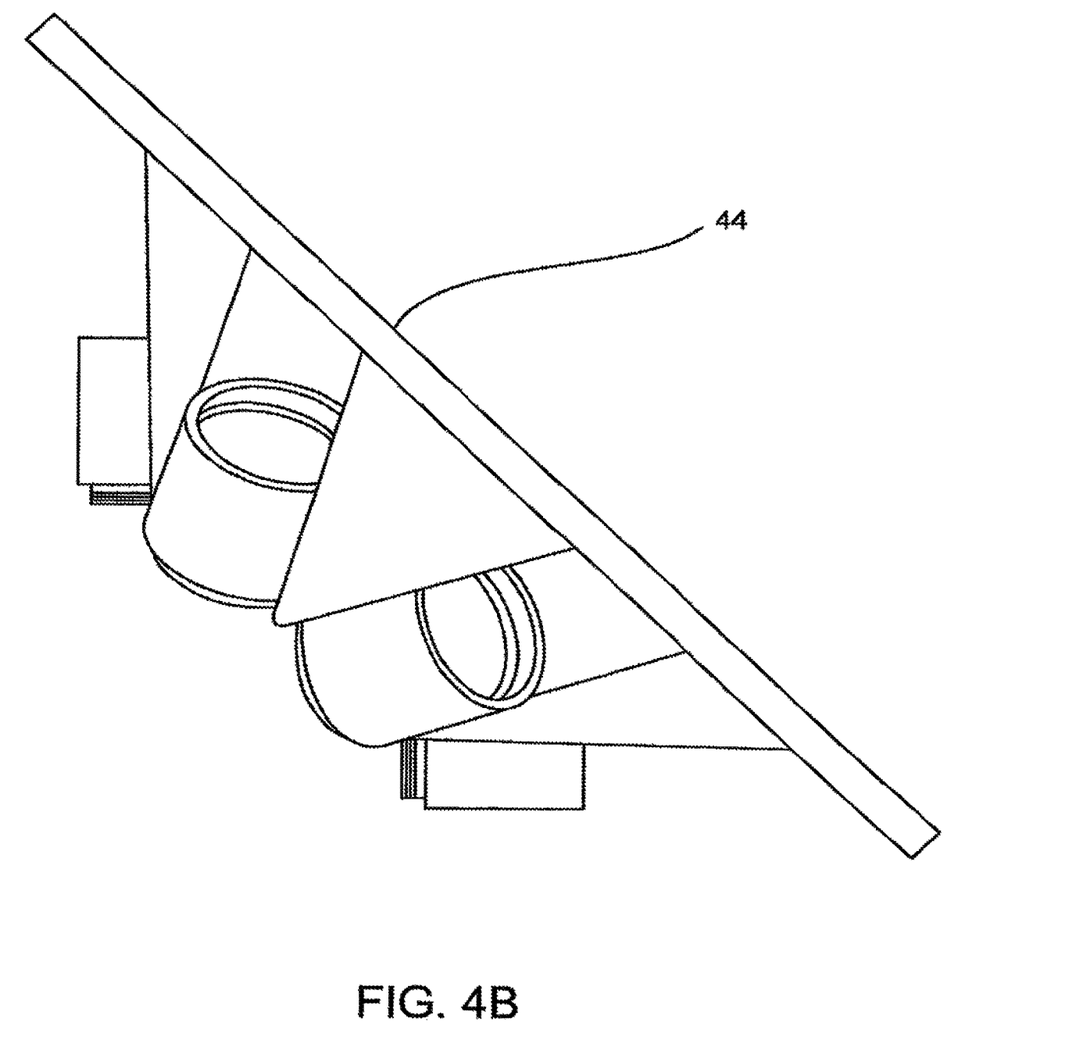
FIG. 4B is a perspective view of an optics system illustrating in phantom the several components of the optics of the system of the invention.
Figure 4C:
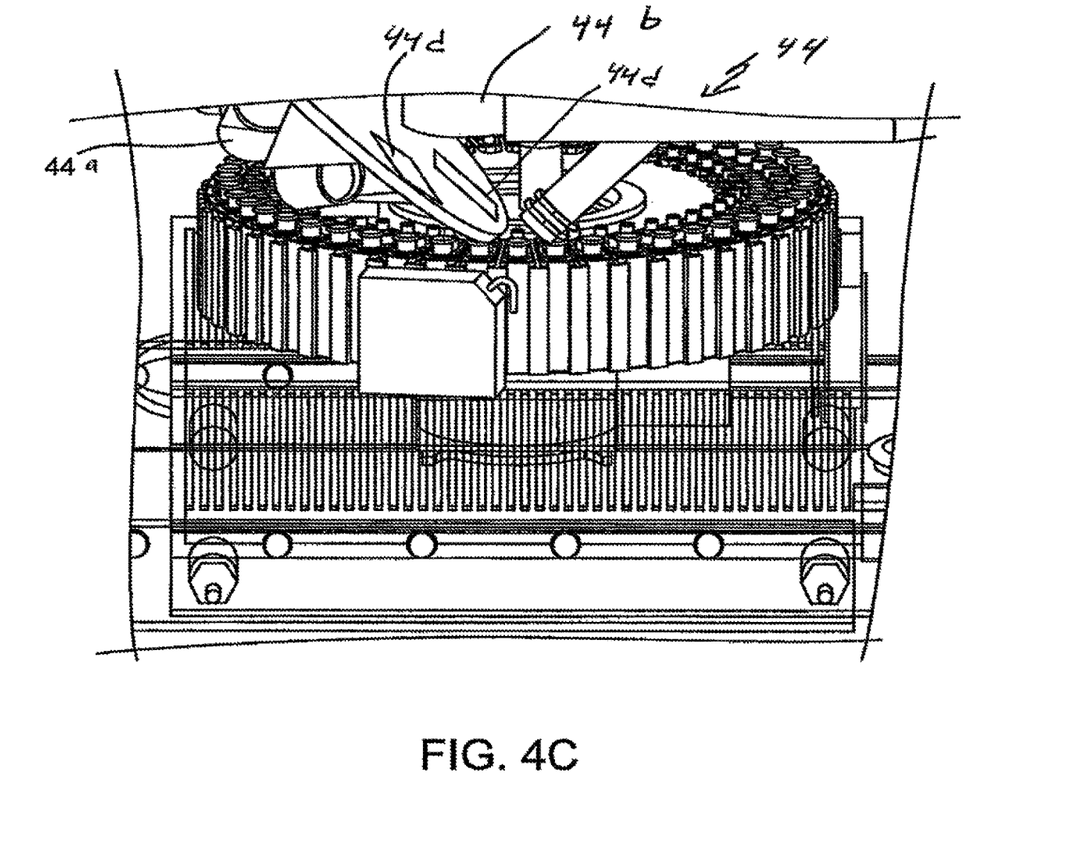
FIG. 4C is an additional perspective view of an optical analyzer illustrating in phantom the several components of the optical analyzer of the system of the invention.

Referring to FIGS. 1-4, the system for conducting the identification of bacteria in urine samples includes a disposable cartridge 12 (FIGS. 1 and 2); a sample processor 14 (FIGS. 3A, 3B, 6 and 7); and an optical analyzer 16 (FIGS. 4A, 4B, and 4C). As shown in FIGS. 1 and 2, cartridge 12 contains four disposable components, which are a centrifuge tube 18, a first pipette tip 20 having a 1 ml volume, an optical cup or cuvette 22, and a second pipette tip 24 having a 0.5 ml volume. It is to be understood that the presently described inventive system is appropriate for the identification of bacteria in any fluid and is not limited to bacteria samples contained in urine.

The centrifuge tube 18 is a container that has an elongated body 18b with a tapered end indicated at 18a. In general, the centrifuge tube 18 initially contains the urine sample and the first pipette tip 20 may be used to dilute the urine-dissolved constitutes, and the second pipette tip 24 may be used to transfer the diluted urine sample into the optical cup or cuvette 22 for optical analysis. The disposable cartridge 12 and its disposable components 18, 20, 22, and 24 may be made of a plastic material which is easily molded and inexpensive to manufacture.

Still referring to FIG. 2, the disposable components 18, 20, 22, and 24 are each contained within separate locations 30, 32, 34, and 36, respectively of the disposable cartridge 12. As is shown, the bottom of compartment 32 which receives and carries the first pipette tip 20 is closed so that any drip from the first pipette tip 20 will not contaminate the surface below the disposable cartridge 12. Each component 18, 20, 22, and 24 is suspended within its respective location 30, 32, 34, and 36 via a lip 40, 42, 46, and 48, respectively attached to each component 18, 20, 22, and 24 which is supported by the top surface 50 of disposable cartridge 12.

Referring to FIGS. 2 and 4A, an optical cup or cuvette 22 may be used in the optical analyzer 16 of FIG. 4A. Preferably, the urine samples are prepared with a saline solution since saline solutions minimize background fluorescence while maintaining the integrity of the bacteria which particularly is important when using optics in the urine analysis process. The optical cup or cuvette 22 will include a reflective coating to assist in the optical analysis. The optical cup or cuvette 22 may be made of an ABS plastic material, glass or a metallic material, e.g., aluminum, and then coated with or layered with the reflective material. Alternatively, in the manufacturing of the optical cup or cuvette 22, the layer of reflective material may be incorporated onto the plastic, glass or metallic material. As best shown in FIG. 2, the optical cup or cuvette 22 includes a tapered end indicated at 22a in order to assist with the optical analysis. It is anticipated that the UV light source in the optical analyzer 16 (FIGS. 4A, 4B and 4C) be directed down the middle of the cup or cuvette 22 for the optical analysis of the urine specimen in the cup or cuvette 22.

Several disposable cartridges 12 each containing the four disposable components 18, 20, 22, and 24 are then inserted into a magazine 26 shown at the top of FIG. 1, which is then loaded into the sample processor 14 as shown in FIG. 3. Magazine 26 contains several disposable cartridges 12 some of which are numbered, each cartridge 12 has a unique bar code as indicated at 28 in FIG. 1 that is paired with the specimen of a patient. Alternatively, the magazine 26 can then be inserted into a device for the optical analysis of the urine samples. Preferably, the same magazine 26 used in obtaining processed urine samples in a sample processor is used in the device for the optical analysis of the processed urine samples.

The sample processor 14 of FIGS. 3A and 3B contains a centrifuge 30, a rotatable gripper mechanism 32 which picks up the centrifuge tube 18 (FIG. 1) of each disposable cartridge 12 and inserts the centrifuge tube 18 into the centrifuge 30; two movable fluid transfer arms 34, 34a which are used to dilute the dissolved material in the urine samples via the pipette tip 20 (FIGS. 1 and 2) and to transfer the diluted sample to the optical cup or cuvette 22 (FIG. 2) via the pipette tip 24; and a syringe pump dispenser fluid system 36 for delivering water to the samples for dilution purposes. The sample processor 14 also includes a drawer 38 which has a rotatable table 40 which receives, supports, and rotates the magazine 26 when the drawer 38 is inserted into the sample processor 14. The drawer 38 contains a magazine drive mechanism (not shown) which rotates the magazine 26.

In general, centrifuge tube 18 contains about 2 ml sample of filtered urine which is placed into the centrifuge tube by the user. This sample may then be sufficiently diluted with a saline solution or water by centrifuging the sample followed by using the first pipette tip 20 with the 1.0 ml volume to decant the supernates in two decant cycles followed by refilling of the centrifuge tube 18 with a saline or water. The second pipette tip 24 having the 0.5 ml volume may then be used to draw out about 500 µl of fluid from centrifuge tube 18 and then to dispense this 500 µl of fluid into the respective optical cup or cuvette 22 of the designated patient. This second pipette tip 24 can then be inserted into the first pipette tip 20 and both pipette tips 20, 24 can be disposed of properly. It is believed that one pipette tip may be used to dilute and draw out instead of two pipette tips. This process may be done manually or may be done automatically.

The loading and unloading of the magazine 26 is accomplished with the several disposable cartridges 12 mounted on the rotatable table 40 (FIG. 1 and FIG. 2). The manual drawer contains a magazine drive mechanism (not shown). Once the magazine 26 is inserted into the sample processor 14, the drive mechanism (not shown) for rotatable table 40 rotates the magazine 26; the bar code reader (element 58 in FIG. 4A) inventories the samples, a level sensor (not shown) verifies that samples were dosed properly; and a second sensor (not shown) verifies that all of the necessary disposable components 18, 20, 22, and 24 (FIG. 2) are contained in each disposable cartridge 12.

The transfer of the centrifuge tube 18 (FIG. 2) into the centrifuge 30 (FIGS. 3A and 3B) will now be described. A centrifuge lid 30a of the centrifuge 30 is oriented to allow the rotatable gripper mechanism unit 32 to access and load the centrifuge 30. The drive mechanism of the rotatable table 40 is configured to align the centrifuge tube 18 of each disposable cartridge 12 into position relative to the rotatable unit 32. The gripper 32a of rotatable gripper mechanism 32 selects the centrifuge tube 18 for transfer from the magazine 26 and into the centrifuge 30. The centrifuge rotor (not shown) is configured to align a vacant centrifuge holder of centrifuge 30 in the load position. The gripper 32a referred to as a "Theta Z gripper" is a radial member that rotates and has a downward and upward movement for picking up and setting a centrifuge tube 18 into a vacant centrifuge holder of centrifuge 30. The lid of centrifuge 30 is closed after all of the centrifuge tubes 18 are placed into the centrifuge 30.

Centrifuge 30 (FIG. 6) is automatically operated to spin the centrifuge tubes 18 at about a 12,000 g-force for about 2 minutes. The centrifuge 30 includes tube holders that are configured to rotate each of the centrifuge tubes 18 about ninety degrees upon rotation of the centrifuge 30. The centrifuge allows for precise positioning and position tracking so that correct tubes are returned to cartridges in the magazine after centrifugation. This action results in the solid formation of the bacteria present in the urine sample at the bottom of the centrifuge tube 18.

There are two fluid transfer arms 34, 34a (FIGS. 3A and 3B) for removing the supernates from two samples of two disposable cartridges 12 at a time. After the two fluid transfer arms 34, 34a (FIGS. 3A and 3B) obtain the pipette tip 20 (FIG. 2) with a 1 ml volume, each of the fluid transfer arms 34 and 34a (FIGS. 3A and 3B) makes two consecutive trips to the centrifuge tube 18, each time drawing fluid from the tube 18 and dispensing this fluid into a waste port (not shown) of sample processor 14 before returning the pipette tip 20 to its location on the disposable cartridge that is being sampled and before continuing with the next sample in the disposable cartridge 12 that is rotated to be registered in the sampling location of sample processor 14.

Figure 7:
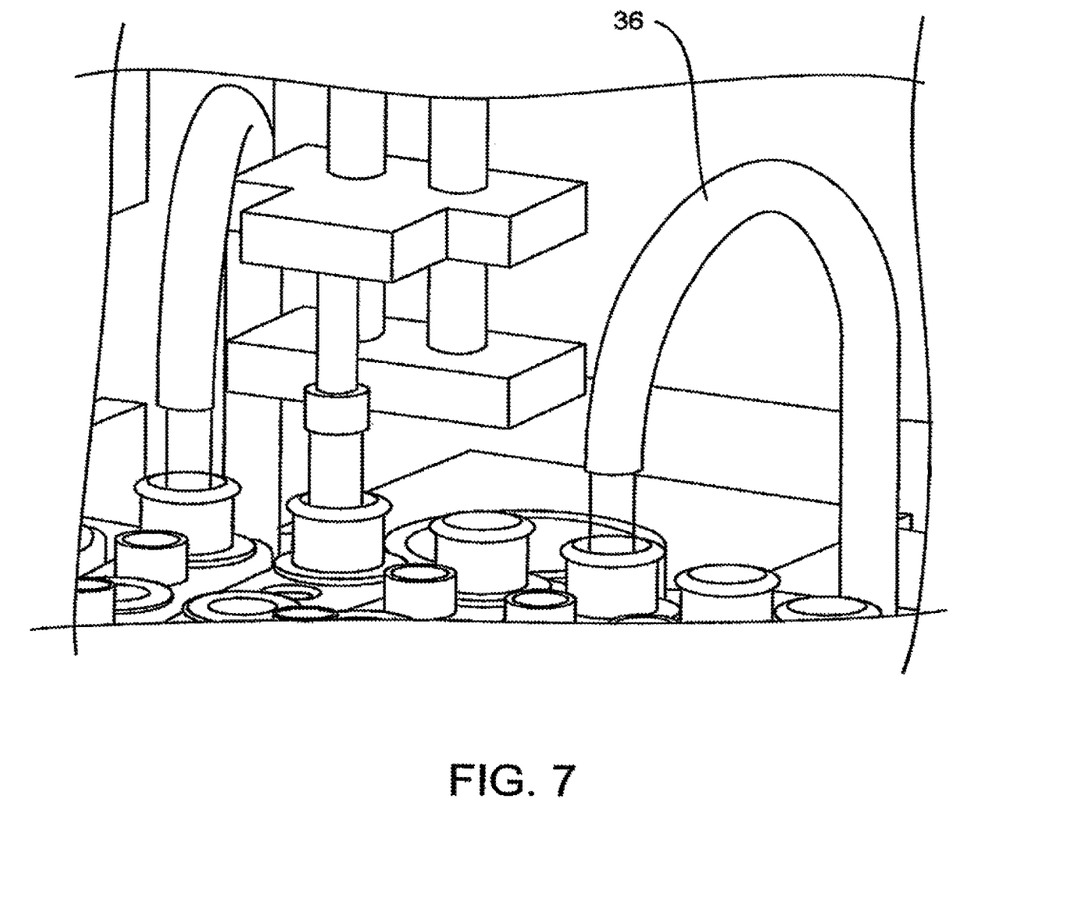
FIG. 7 is an additional perspective view of a sample processor illustrating in phantom the several components of the sample processor of the system of the invention.

The syringe pump dispenser fluid system 36, is illustrated in FIG. 7, for delivering water or saline to the samples for dilution purposes. The waste fluid which had been decanted from a centrifuge tube 18 as described in the preceding paragraph is replaced with clean process fluid via system 36. Two syringe pumps dispense this clean process fluid into the centrifuge tube 18 from which the waste fluid had been removed in the previous step. During the final refill step, a smaller amount of clean fluid is used in order to get the bacteria level in the cartridge tube 18 to the required concentration.

After the sample in centrifuge tube 18 has been sufficiently diluted with the clean fluid, one of the two fluid transfer arms 34, 34a (FIGS. 3A and 3B) transfers the processed sample in centrifuge tube 18 to the optical cup or cuvette 22 of its respective disposable cartridge 12. One of the fluid transfer arms 34, 34a grasps the pipette tip 24 having the 0.5 ml volume, which until now has not been used in this process. This pipette tip 24 with the smaller volume is used to draw out about 500 µl of fluid from centrifuge tube 18 and is used to dispense this fluid into the respective optical cup or cuvette 22 of the designated patient. This pipette tip 24 with the smaller volume is then inserted into the pipette tip 20 with the larger volume via the fluid transfer arm 34 or 34a for disposal of both pipette tips 20, 24.

The metering/decanting, metering/refilling, and metering/fluid transferring process described herein above is to obtain preferably, approximately a 1,000,000:1 dilution of the dissolved materials retaining bacteria in the urine sample in centrifuge tube 18. This can be achieved by 1) centrifuging, through means known to those skilled in the art, the urine sample at a 12,000 g-force; 2) decanting about 95% of the fluid by using the first pipette tip 20; 3) replacing the decanted solution of 2) with a saline solution; and 4) repeating steps 1), 2), and 3) at least five times by using the first pipette 20. The final processed urine sample in centrifuge tube 18 can then be decanted via the second pipette 24 into the optical cup or cuvette 22.

The final processed urine sample in optical cup or cuvette 22 can then be used in an optical analysis for determining the micro-organism's identity and/or quantity in the urine sample in optical cup or cuvette 22. This information can be obtained by using the system as disclosed in the aforesaid U.S. Publication No. 2007/0037135 A1.

Each of the steps described above for one centrifuge tube 18 is done in the sample processor 14 for each of the disposable cartridges 12 in magazine 26. It is to be appreciated that the waste fluid of each disposable cartridge 12 is disposed into a receptacle (not shown) in sample processor 14 or is plumbed directly into a drain. The waste disposables, i.e., the disposable cartridge 12 and disposable components 18, 20, 22, and 24 remain on the magazine 26 for manual removal when the magazine 26 is unloaded in preparation for the next operation of the sample processor 14 for processing the next batch of urine samples.

The following steps are involved in processing the urine samples in preparation for analysis via the optical analyzer 16 of FIGS. 4A, 4B, and 4C. In general, a sample of urine is obtained in a test tube. This sample is passed through a ten micron filter from which a 2 ml sample is obtained and placed into the centrifuge tube 18. The desired diluted sample, i.e., 1,000,000:1 dilution of dissolved materials while retaining bacteria in the urine sample is obtained by centrifuging this 2 ml sample at about a 12,000 g-force; and decanting 95% of the fluid. This latter step is repeated five times wherein the decanted solution is replaced each time with a saline solution. A saline solution is selected for this process in that it minimizes background fluorescence which comes into play when the processed urine sample is inserted into the optical analyzer 16 while maintaining the bacteria integrity.

The optical analyzer 16 of FIGS. 4A, 4B, and 4C will now be described. With reference to FIG. 4A, the optical analyzer 16 includes an optics system 44 (shown in greater detail in FIGS. 4B and 4C), a thermal control unit (not shown), a drawer 50 which has a rotatable table 52 which receives, supports, and rotates a magazine 54 containing a plurality of holders 56 for receiving the disposable cartridges 12 in which cups or cuvettes 22 contain the processed urine samples which are to be analyzed, and a bar code reader 58 (FIG. 4A).

As can be appreciated, a cartridge 12 that has the cups or cuvettes 22 containing the processed urine sample for optical analysis are placed into the holders 56 of the magazine 54. FIG. 4A illustrates the magazine 54 mounted on the rotatable table 52 being loaded into the optical analyzer 16. Drawer 50 is pulled out manually for the loading and unloading of magazine 54. Drawer 50 contains the thermal control unit (not shown) and a drive mechanism (not shown). Alignment features on the magazine 54 and drawer 50 allow the operator to orient the magazine 54 properly on the drive mechanism and the thermal control unit when the magazine 54 is loaded onto the rotatable table 52. Once the drawer 50 and magazine 54 are manually inserted into the optical analyzer 16, the drive mechanism rotates the magazine 54 at which time a bar code reader station 58 (FIG. 4A) inventories the samples. A level sensor (not shown) verifies that each optical cup or cuvette 22 contains the correct sample volume. An operator can access the optical analyzer 16 when a user interface indicates that all the samples in the cups or cuvettes 22 have been analyzed and drawer 50 is prevented from being opened when any of the components of optical analyzer 16 are moving or when the UV light sources of the optics system 44 are on.

FIG. 4A illustrates the magazine 54 on rotatable table 52 while being positioned within optical analyzer 16. The optical analyzer 16 further includes a mechanical locking system (not shown) which positions the drawer 50 accurately with respect to the optics system 44. The drive mechanism is configured to automatically rotate the magazine 54 to position each cartridge 12 into the bar code reader station 58 and into precise alignment with the optics system 44. A second mechanical locking system (not shown) is used to secure each cup or cuvette 22 in its proper positioning relative to the optics system 44 for optical analysis.

FIG. 4A illustrates the thermal control for the optical cups or cuvettes 22. Preferably, the temperature of each cup or cuvette 22 is decreased to a temperature which will slow the metabolism of the bacteria while increasing the fluorescence signal. The thermal control unit 46 which is a thermal electric cooler (TEC) cools a large thermal mass 60 which is located on the rotatable table 52 underneath the magazine 54. The thermal mass 60 (FIG. 4A) is in direct contact with the optical cups or cuvettes 22, and an infrared temperature sensor (not shown) detects and monitors the temperature of each sample prior to the sample being rotated and positioned within the optics system 44.

The optics system 44 of the optical analyzer 16 will now be described. The optics system is shown in greater detail in FIG. 4B. The optics system 44 contains three separate units, that is, an excitation unit 44(a), an optical collection unit 44(b) and a spectrometer. Excitation will be provided by a ultra-violet (UV) light source, which preferably will be LED (light emitting diode). A series of five LED modules provide an excitation unit 44(a) will sequentially provide excitation signals to each sample cup or cuvette 22 at five different excitation wavelengths which will be applied to each sample cup or cuvette 22 in the same order. The excitation time will be approximately 14 seconds per wavelength. The excitation emissions are directed via lenses and filters 44(d) to be directed an upper surface of the sample in the cuvette 22 as shown in FIG. 2. In order to narrow or control the shape of each excitation wavelength, narrow bandwidth filters will be used. These filters will direct in a downwardly direction the excitation wavelengths E to the sample cups or cuvettes 22 and the fluorescent emissions F will be reflected back in an upwardly direction to the optical collection unit from the same position of the cassette. The fluorescent emissions can be separated and directed via a filter arrangement. FIG. 4C illustrates the positioning of the optics system 44. As described previously, mechanical locking features position the drive mechanism such that the sample cup or cuvette 22 is aligned precisely. This precise alignment allows for the reflection of the fluorescent emission to the optics system 44 allowing for measurement of fluorescence. Optical elements (not shown) are utilized to gather and direct the fluorescent emissions into the spectrophotometer for measurement.

In addition, the optical collection unit includes optical elements to gather and direct the fluorescent emissions of the samples in the cups or cuvettes 22 into the spectrometer.

Figure 5:
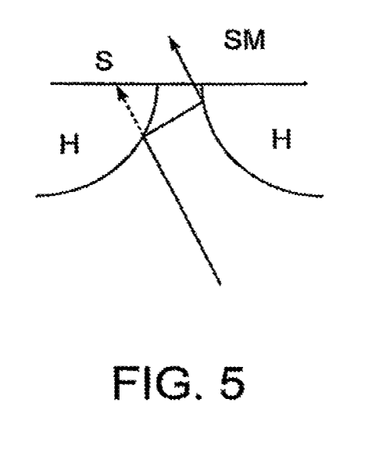
FIG. 5 is a schematic illustrating mirrored convex "horn" that may be provided at the entrance of a slit of a spectrometer.
Figure 6:
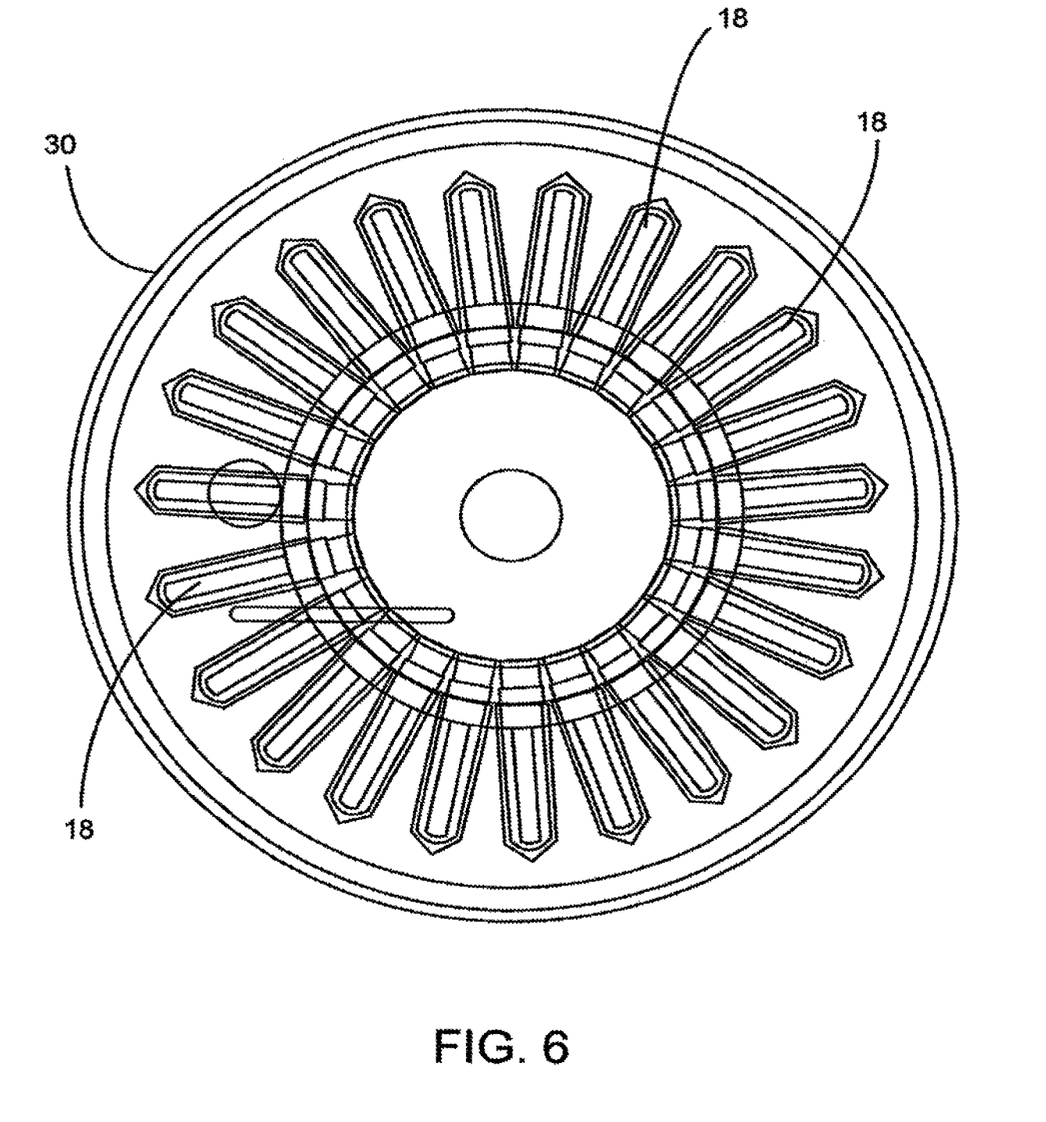
FIG. 6 is a perspective view of a centrifuge illustrating in phantom the several components of the centrifuge of the system of the invention.

The optics system 44 may include a Czerny-Turner spectrometer with a CCD (charged couple device) Photon Detector, whereby fluorescent photons are reflected by several mirrors before contacting the CCD device. The emitted fluorescence will be monitored on the CCD device by integrating for a period of time. It is also envisioned that the Czerny-Turner spectrometer be modified with additional cylindrical lenses adjacent the entrance slit and the CCD device in order to improve photon usage efficiency. Additionally, as schematically illustrated in FIG. 5, mirrored convex "horn" H may be provided at the entrance of the slit S of the spectrometer SM to direct additional photons through the slit S.

Referring to FIG. 4A, the optics system 44 will include a light-tight enclosure or housing 64 in order to minimize light entering the optics system 44, and the camera of the CCD device will include a thermal electric cooler (TEC) (not shown) for transferring heat from the camera chip to the enclosure or housing 64 of the optics system 44.

Both the sample processor 14 and the optical analyzer 16 will have a HEPA air-filtering system for ventilation purposes in filtering the air entering and exiting the sample processor 14 and the optical analyzer 16. The sample processor 14 and the optical analyzer 16 will also have a slight positive pressure during operation. However, this pressure will decrease to atmospheric pressure when the user is allowed to open the door. Power to both the sample processor 14 and the optical analyzer 16 will be supplied from a separate rack mounted power supply module.

It is further envisioned that the LED intensity will be monitored to correlate the emitted fluorescence with the intensity of the excitation fluorescence. In particular, the information obtained by the optical analyzer 16 may be used to generate graphs similar to FIGS. 5 through 9 of U.S. Publication No. 2007/0037135 A1, described in greater detail below. The graphs represent for the concentration of the bacteria in the sample cups or cuvettes 22, the fluorescence intensity, the emission wavelengths and the excitation wavelengths.

As discussed hereinabove, the optical analyzer 16 provides results that are then used to identify the type of bacteria in the urine samples. This can be done by coupling the optical analyzer 16 to a computer module (not shown) and feeding in the acquired information of the optical analyzer 16, such as the fluorescence emission, into the computer module. The computer module may perform multivariate analysis on the fluorescence excitation-emission matrices of the urine samples to identify and quantify the urine samples in a manner similar to that disclosed in the above U.S. Publication No. US 2007/0037135 A1. Here, the system includes a fluorescence excitation module which includes an excitation light source, a sample interface module for positioning the sample to receive the light source, a fluorescence emission module and a detection device. The computer module described above is coupled to the fluorescence module. The multivariate analysis may comprise extended partial least squared analysis for identification and quantification of the urine samples.

It is still further envisioned that a "homogenitor tube" will be used to mix the different LED packages output into a uniform UV light source. A typical "homogenitor tube" for use in the invention will be similar to that known to those skilled in the art.

The present invention has been described with reference to the preferred embodiments. Obvious modifications and alterations will occur to others upon reading and understanding the preceding detailed description. It is intended that the invention be construed as including all such modifications and alterations.

The invention claimed is:

1. A sample processor for preparing fluid samples used for conducting the identification and quantification of microorganisms in the urine samples, comprising:
   a) a rotatable table; and
   b) a magazine supported by the rotatable table;
   c) a plurality of cartridges located within the magazine;
   d) a plurality of disposable components including an optical cup or cuvette located within the plurality of cartridges, the optical cup or cuvette containing a fluid sample; and
   e) an optical analyzer located above the magazine, wherein the optical analyzer includes an optics system for analyzing each fluid sample, wherein
   the optical cup or cuvette comprises a container having an open portion through which a light travels for the optical analysis of the fluid sample, said container including a reflective surface for enhancing the optical analysis, said container having a sidewall that is continuously tapered along its length to a truncated conical end, wherein during optical analysis, the light is directed downwardly through the open portion of the container and into the fluid sample, wherein the tapered sidewall is configured to assist with the optical analysis and the reflective surface of the container reflects fluorescent emissions back in an upwardly direction out of the fluid sample and through the open portion of the container to an optical collection unit for optical analysis.

2. The sample processor of claim 1, wherein the fluid sample is urine.

3. The sample processor of claim 1, further comprising a rotatable gripper.

4. The sample processor of claim 1, further comprising a movable fluid transfer arm for diluting the dissolved material in the fluid samples and for transferring the diluted fluid urine to the optical cup or cuvette of each cartridge.

5. The sample processor of claim 1, further comprising a syringe pump dispenser fluid system for delivering clean fluid to the fluid samples for the dilution of the dissolved materials in the fluid samples.

6. The sample processor of claim 1, further comprising a waste passageway for removing waste from the fluid sample and for concentrating the fluid containing the micro-organism.

7. The sample processor of claim 6, wherein the waste passageway is defined in a pipette tip.

8. An optical analyzer for analyzing fluid samples, comprising:
   a) a drawer having a rotatable table and a magazine supported by the rotatable table;
   b) a plurality of cartridges with cups or cuvettes, each containing a fluid sample, the plurality of cartridges located within the magazine; and
   c) an optics system located above the magazine for analyzing each fluid sample, wherein the optical cup or cuvette comprises a container having an open portion through which a light travels for the optical analysis of the fluid sample, said container including a reflective surface for enhancing the optical analysis, said container having a sidewall that is continuously tapered along its length to a truncated conical end, wherein during optical analysis, the light is directed downwardly through the open portion of the container and into the fluid sample, wherein the tapered sidewall is configured to assist with the optical analysis and the reflective surface of the container reflects fluorescent emissions back in an upwardly direction out of the fluid sample and through the open portion of the container to an optical collection unit within the optics system for optical analysis.

9. The optical analyzer of claim 8, further comprising a bar code reader station.

10. The optical analyzer of claim 8, further comprising a thermal control located under the rotatable table and configured to decrease and maintain the temperature of each fluid sample to slow the metabolism of the bacteria while increasing the fluorescence signal.

11. The optical analyzer of claim 9, further comprising a drive mechanism for automatically rotating and registering the rotatable table and the plurality of cartridge with cups or cuvettes in position relative to the bar code reader station and the optics system.

12. The optical analyzer of claim 8, further comprising a first mechanical locking system for maintaining the drawer in position relative to the optics system.

13. The optical analyzer of claim 8, further comprising a second mechanical locking system for maintaining each cup or cuvette in position relative to the optics system.

14. The optical analyzer of claim 8, wherein the optics system is comprised of an excitation module unit, the optical collection unit and a spectrometer.

15. The optical analyzer of claim 14, wherein the optical collection unit is a CCD photon detector; and wherein the spectrometer is a Czerny-Turner spectrometer.

16. The optical analyzer of claim 14, wherein the fluid sample is urine.

17. The optical analyzer of claim 14, wherein the spectrometer includes an entrance slit and cylindrical lenses located adjacent to the entrance slit.

18. The optical analyzer of claim 8, further comprising a thermal control to maintain the temperature of each fluid sample.

* * * * *